(12) United States Patent
Brückler et al.

(10) Patent No.: US 9,333,004 B2
(45) Date of Patent: May 10, 2016

(54) MEDICAL INSTRUMENT WITH A CONTOURED AXLE PIN

(75) Inventors: Hubert Brückler, Tuttlingen (DE); Jürgen Dresp, Tuttlingen (DE); Martin Blocher, Tuttlingen (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 2157 days.

(21) Appl. No.: 11/289,167

(22) Filed: Nov. 29, 2005

(65) Prior Publication Data

US 2006/0224182 A1 Oct. 5, 2006

(30) Foreign Application Priority Data

Mar. 31, 2005 (DE) .................... 20 2005 005 406 U (51) Int. Cl.
| | | |
|---|---|---|
| A61B 17/00 | (2006.01) | |
| A61B 17/32 | (2006.01) | |
| A61B 18/14 | (2006.01) | |
| A61B 17/29 | (2006.01) | |
| A61B 18/00 | (2006.01) | |
| A61B 19/00 | (2006.01) | |

(52) U.S. Cl.
CPC ..... *A61B 17/320016* (2013.01); *A61B 18/1445* (2013.01); *A61B 2017/2929* (2013.01); *A61B 2017/2939* (2013.01); *A61B 2018/00589* (2013.01); *A61B 2018/146* (2013.01); *A61B 2019/4868* (2013.01)

(58) Field of Classification Search
CPC ............... A61B 17/320016; A61B 18/1445; A61B 2017/2929; A61B 2017/2939; A61B 2018/00589; A61B 2018/146; A61B 2019/4846; F16B 33/002

USPC ......... 606/205, 207, 208; 7/160; 30/123, 254; 411/166, 338
See application file for complete search history.

(56) References Cited

U.S. PATENT DOCUMENTS

| | | | | |
|---|---|---|---|---|
| 535,828 | A | * 3/1895 | Hagon | ........................ 411/144 |
| 938,376 | A | * 10/1909 | Friday | .............................. 30/177 |
| 1,715,975 | A | * 6/1929 | Angell | .............................. 411/81 |
| 4,233,979 | A | * 11/1980 | Naser | ................................ 606/1 |
| 4,380,238 | A | 4/1983 | Colucci et al. | |
| 5,267,400 | A | * 12/1993 | Danube et al. | .................. 30/250 |
| 5,813,146 | A | * 9/1998 | Gutkowski et al. | ............... 36/97 |
| 5,968,074 | A | 10/1999 | Prestel | |

(Continued)

FOREIGN PATENT DOCUMENTS

| | | |
|---|---|---|
| DE | 297 13 150 U1 | 7/1997 |
| DE | 695 31 896 T2 | 8/2004 |

(Continued)

OTHER PUBLICATIONS

Catalogue "Laparoscopy", 5th edition Jan. 2004, par. 4 "Präparier- und Fasszangen" and Par. 5 "Scheren, Stanzen, Zangen für Probeexcision".

*Primary Examiner* — Kathleen Holwerda
*Assistant Examiner* — Sarah Simpson
(74) *Attorney, Agent, or Firm* — Whitmyer IP Group LLC (57) ABSTRACT

A medical instrument has a distal end area on which jaw parts are arranged which are movable relative to one another and pivotable about an axle pin. Said axle pin is received in an opening in said medical instrument. Said axle pin comprises a head which is non-circular, and the opening has a contour corresponding to the head.

8 Claims, 5 Drawing Sheets

(56) References Cited

U.S. PATENT DOCUMENTS

| | | | |
|---|---|---|---|
| 6,018,875 A * | 2/2000 | Miranda | 30/233 |
| 6,041,823 A * | 3/2000 | Kusama | 138/99 |
| 6,063,103 A * | 5/2000 | Hashiguchi | 606/205 |
| 6,096,058 A * | 8/2000 | Boche | 606/205 |
| 6,309,404 B1 * | 10/2001 | Krzyzanowski | 606/208 |
| 6,458,130 B1 * | 10/2002 | Frazier et al. | 606/51 |
| 6,585,735 B1 * | 7/2003 | Frazier et al. | 606/51 |
| 7,024,967 B1 * | 4/2006 | Cheng | 81/60 |
| 2004/0044363 A1 * | 3/2004 | Fowler | 606/205 |
| 2005/0222611 A1 * | 10/2005 | Weitkamp | 606/205 |
| 2005/0251946 A1 * | 11/2005 | Heinrich et al. | 15/250.32 |
| 2007/0021777 A1 * | 1/2007 | Fowler | 606/205 |
| 2007/0106304 A1 * | 5/2007 | Hammack et al. | 606/113 |

FOREIGN PATENT DOCUMENTS

| | | | |
|---|---|---|---|
| EP | 0 773 743 B1 | | 8/1995 |
| WO | WO-2006/029660 | * | 10/2004 ............ F16B 13/06 |

* cited by examiner

MEDICAL INSTRUMENT WITH A CONTOURED AXLE PIN

CROSS-REFERENCE TO RELATED APPLICATIONS

This application claims priority of German Patent Application No. 20 2005 005 406.2 filed on Mar. 31, 2005.

BACKGROUND OF THE INVENTION

The invention relates to a medical instrument with a distal end area on which jaw parts are arranged which are movable relative to one another and pivotable about an axle pin, said axle pin being received in an opening of the medical instrument.

Medical instruments of this kind, for example dissecting forceps, grasping forceps, and scissors, are marketed by the Applicant.

Various versions of these medical instruments are described in the catalog "Laparoskopie" [Laparoscopy] from the same company (5th edition January 2004, section 4 entitled "Präparier-und Fasszangen" [Dissecting forceps and grasping forceps] and section 5 entitled "Scheren, Stanzen, Zangen für Probeexcision" [Scissors, punches and forceps for excision of samples]).

The abovementioned medical instruments are used in the field of minimally invasive surgery.

In laparoscopy and thoracoscopy, the minimally invasive versions of operations on the gallbladder, cecum and esophagogastric junction, in treatment of reflux disease and inguinal hernia, and in surgery of the joints and spinal column, have proven best.

In all these techniques, the operations are performed through relatively small openings. The surgeon's view is in this case afforded by use of endoscopes, which can be connected to a video chain and thus permit telesurgery. The extremely small accesses with incisions of 5 to 10 millimeters demand the use of slender instruments.

The medical instruments used in minimally invasive surgery have a structure made up of several parts.

Medical scissors for minimally invasive surgery usually comprise a shaft measuring approximately 30 to 50 cm in length. Arranged at the proximal end of this shaft there is a scissor-like handle which is connected to the jaw parts, arranged at the distal end, by way of a rod-shaped actuating element displaceable in the interior of the shaft.

At the distal end area, a toggle mechanism, for example, is connected to the rod-shaped actuating element. This toggle mechanism transmits the pushing and pulling forces to jaw parts, which are movable relative to one another, or, more precisely, are mounted pivotably about an axle pin extending transversely with respect to the longitudinal axis of the shaft. Designs in the form of grasping, gripping or cutting instruments are known, including those for electrocoagulation.

Since the instruments in minimally invasive surgery are inserted into the body through trocars, the clear internal diameter of the trocar sleeve engaged in the body determines the size of the components of the medical instruments, for example the length of the transversely extending axle pin.

Moreover, the medical instruments should be reusable. During their use, smaller components in particular often have to be able to cope with considerable stresses.

The forces which can arise during dissection, cutting and resection, for example if the operating surgeon strikes the instrument against bone, have to be taken up in an optimal manner by the axle pin and carried to the medical instrument.

The same applies to pressing and pulling forces which are applied to the axle pin by the scissor-like handle via the rod-shaped actuating element.

The small dimensions of the axle pin, of only about 5 mm length and about 1 mm diameter, therefore mean that a particular structure is desirable for taking up and transmitting forces.

The medical instruments should also have no niches in which bacteria can gather. They must be easy to dismantle for mechanical or manual cleaning and, in addition, must be able to be completely sterilized in modern autoclaving procedures.

In the course of cleaning and sterilizing of the medical instruments, smaller components are once again exposed to considerable stresses. During the mechanical or manual cleaning of the instruments, mechanical influences may arise, such as impacts or pressure loads and tensile loads. Moreover, in standard protocols used today in modern flash autoclaving, the individual components have to withstand temperature jumps and high temperatures of up to 165° C. with saturated live steam. Resistance to various forms of corrosion is therefore a prerequisite.

Fragmenting, for example, of parts or all of the axle pin must be avoided under all circumstances, both for reasons concerning reliability for the user and also concerning the safety of the patient being treated, since fragments remaining in the patient's body can cause health problems.

The known medical instruments employed usually have a rivet with a circular head as their axle pin.

In practice, it has now been found that the axle pin with a circular head may come loose during the use of the medical instrument and turn about its own axis. This turning about its own axis intensifies during further use, such that the axle pin becomes worn and widens its path. Dirt traps thus form which can be accessed only with difficulty for cleaning. In addition, optimal handling of the medical instrument is no longer possible. Necessary repairs then in most cases entail complete replacement of damaged components. Lateral slipping not only leads to unreliability of function but also possibly to the jaw parts falling off, which would cause serious problems during an operation.

It is therefore an object of the present invention to remedy this situation and to develop a medical instrument of the stated type in such a way that it has an axle pin whose function is reliably maintained on a permanent basis.

SUMMARY OF THE INVENTION

According to the invention, the object is achieved by the fact that the axle pin comprises a head which is noncircular, and the contour of the opening corresponds to the head.

These measures have the advantage that the axle pin is received with an exact fit in a recessed opening and is thus secured against rotation. If the axle pin is exposed to considerable forces, for example because of the jaw parts striking against hard cartilaginous or osseous tissue, the noncircular shapes of the axle pin head, more precisely the lateral edges of the axle pin head, provide mechanical resistance to these forces, and this prevents turning. The form-fit engagement between the noncircular contour and the correspondingly contoured opening means that torsional forces acting on the axle pin are better carried away. These torsional forces do not cause any turning of the axle pin relative to the instrument, and in the long term they do not cause loosening of the axle pin's fit. The formation of gaps which act as niches for bacteria is thus permanently excluded.

In a further embodiment of the invention, the head of the axle pin is configured as a polygon.

This measure has the advantage that the forces taken up by the axle pin can be carried off to the medical instrument via the lateral edges of the polygonal head.

In a further embodiment of the invention, the corners of the polygon are rounded.

This measure has the advantage that deformation or stripping of the rounded corners under loading is avoided, and the rounded corners give the head increased stability.

In a particular embodiment, the polygon is a triangle.

This measure has the considerable advantage that a triangular head of the axle pin is a stable, small and compact body which has relatively long edges for force transmission. The three edges of the triangle permit, using a small compact body, relatively long contact edges for transmission of torsional forces to the medical instrument. Moreover, the rounded edges prevent the points of the triangle being sheared off under the effect of high torsional forces, so-called notch forces, and thereby increase the mechanical stability of the axle pin. The geometry of the triangle thus represents an optimal compromise between the space requirements of the body, the length of its contact edges, its compactness and its noncircular geometry.

In a further embodiment of the invention, the triangle is equilateral.

This measure has the advantage that the force can be carried off uniformly via all edges of the triangle.

In another embodiment of the invention, the axle pin is made up of at least two components which can be joined to one another.

This measure has the advantage that assembly is made easier and a firm connection is made possible acting in the direction of the longitudinal axis of the axle pin. At least some parts of the axle pin can also be made of an insulating material, so as to be able to use the preferred form of the axle pin also in medical instruments for electrocoagulation.

In another embodiment of the invention, at least one of the components comprises a head which is noncircular.

This measure has the advantage that, in the case of a multi-part axle pin, the securing against rotation of the entire axle pin is guaranteed by at least one of the components.

In another embodiment of the invention, the multi-part axle pin comprises a bushing and a bolt which can be inserted into the latter.

This measure has the advantage that it is possible to use a bushing made of insulating material, for example ceramic, in which the bolt is received in an insulated manner, and an axle pin is thus obtained which can be used in medical instruments for electrocoagulation.

In another embodiment of the invention, bolt and bushing can be screwed together.

This measure has the advantage that bolt and bushing are connected to one another in a captive manner. In the case specifically of a ceramic bushing, the bushing can be pressed or riveted to the bolt, this representing an alternative possibility to screwing.

In another embodiment of the invention, bolt and bushing can be pressed or riveted together.

This measure has the advantage of ensuring a firm connection of bushing and bolt in the axial direction of the axle pin. Separation of the riveted parts is possible only if the axle pin is destroyed. It also proves advantageous that, by being pressed or riveted together, the bolt and bushing are better able to fit the contours of the openings.

In another embodiment of the invention, a tightening nut is provided which can be placed between bolt and bushing in order to connect these to one another in a captive manner.

This measure has the advantage that the function of the medical instrument can already be checked during assembly, thus facilitating the assembly procedure. After the bolt has been inserted into the bushing, the hinge mechanism of the jaw parts or the fit of the noncircular head can be tested. Following this test of the instrument's function, the components can finally be connected to one another by screwing with the tightening nut.

In another embodiment of the invention, both joinable components of the axle pin comprise a noncircular head.

This measure has the advantage that the force is carried by the axle pin to the medical instrument at several contact sites of the axle pin or contact sites of the heads of the axle pin. This leads to a more stable and more resistant design of the axle pin.

In another embodiment of the invention, the distal end area of the medical instrument is designed as a fork head in whose opposite outer faces recessed openings are formed into which the heads of the two components can be received.

This measure has the advantage that, first, by means of the heads of the two components being received in the recessed openings, the axle pin is secured against rotation on both sides, and, secondly, the forces that occur can be carried off in an optimal manner via a fork-head-shaped distal end area of the medical instrument.

In another embodiment of the invention, the recessed depth of the openings corresponds to the height of the heads.

This measure has the advantage that the heads are received flush in the openings. In this way, it is possible to obtain almost smooth surfaces on the instrument in the area of the axle pin, so as to avoid accumulation of blood or tissue residues. Moreover, this way of receiving the axle pin is extremely desirable and advantageous since it means that, during the operation, the instrument does not become caught via protruding corners or edges in the distal end area.

It will be appreciated that the features mentioned above and those still to be explained below can be used not just in the cited combinations, but also in other combinations or singly, without departing from the scope of the present invention.

BRIEF DESCRIPTION OF THE DRAWINGS

The invention is described and explained in greater detail below on the basis of a selected illustrative embodiment and with reference to the attached drawings, in which.

DETAILED DESCRIPTION OF THE INVENTION

In FIGS. 1 to 6, a medical instrument for minimally invasive surgery is designated in its entirety by reference number 10.

Figure 1:
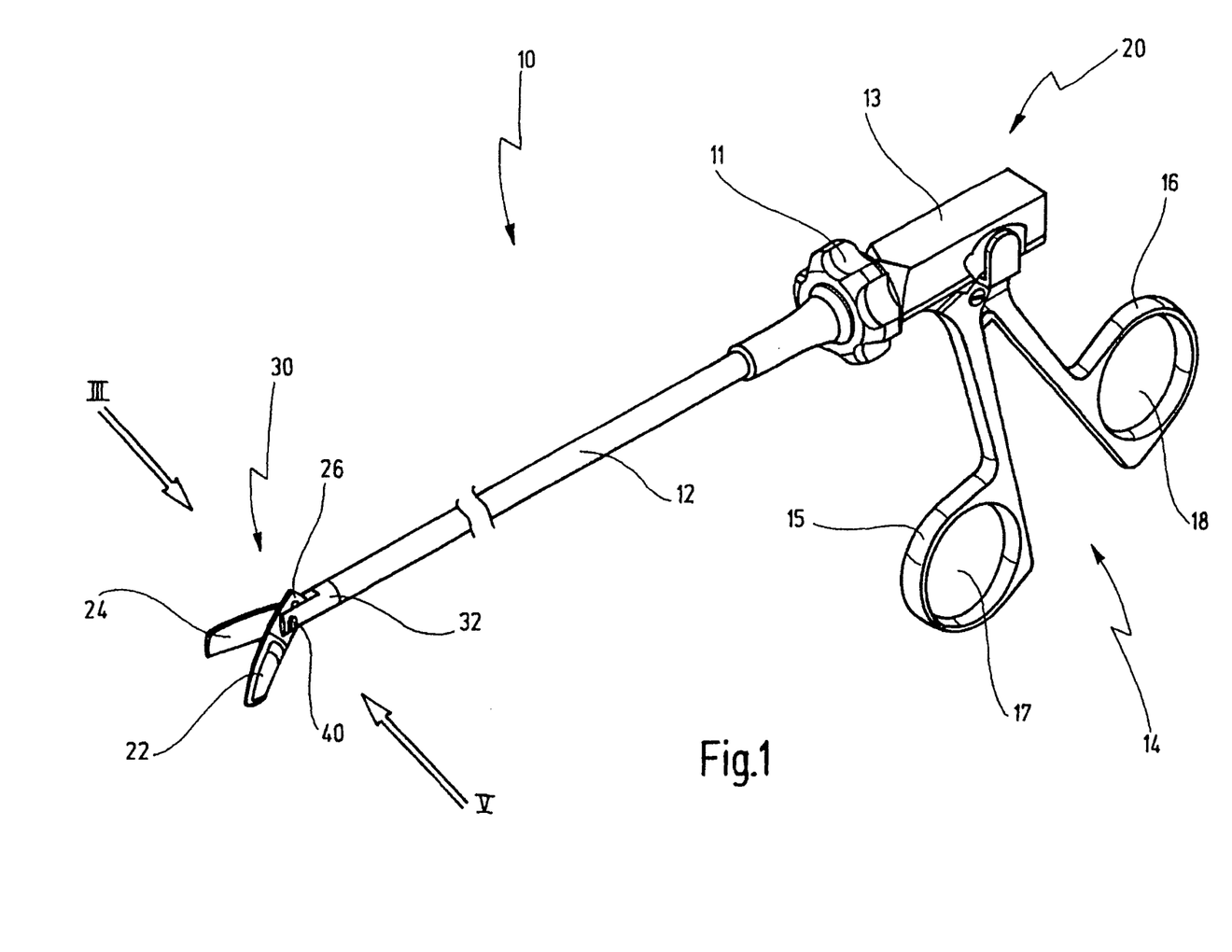
FIG. 1 shows a perspective view of a surgical instrument according to the invention configured as scissors for minimally invasive surgery.

The medical instrument 10 has a shaft 12 on whose proximal end area 20 an adjustment wheel 11 is fixedly connected. This fixedly connected adjustment wheel 11 has indents provided for the fingers of the human hand. The shaft 12 can turn with this adjustment wheel 11 about its own axis.

At the proximal end, the shaft 12 is secured on a housing 13, and a handle 14 is provided on this housing 13. This handle 14 has scissor-like grip parts 15, 16. The grip part 15 is in this case stationary, and the other grip part 16 is movable.

Moreover, each of these grip parts 15, 16 has an oval finger aperture 17, 18, respectively.

Figure 2:
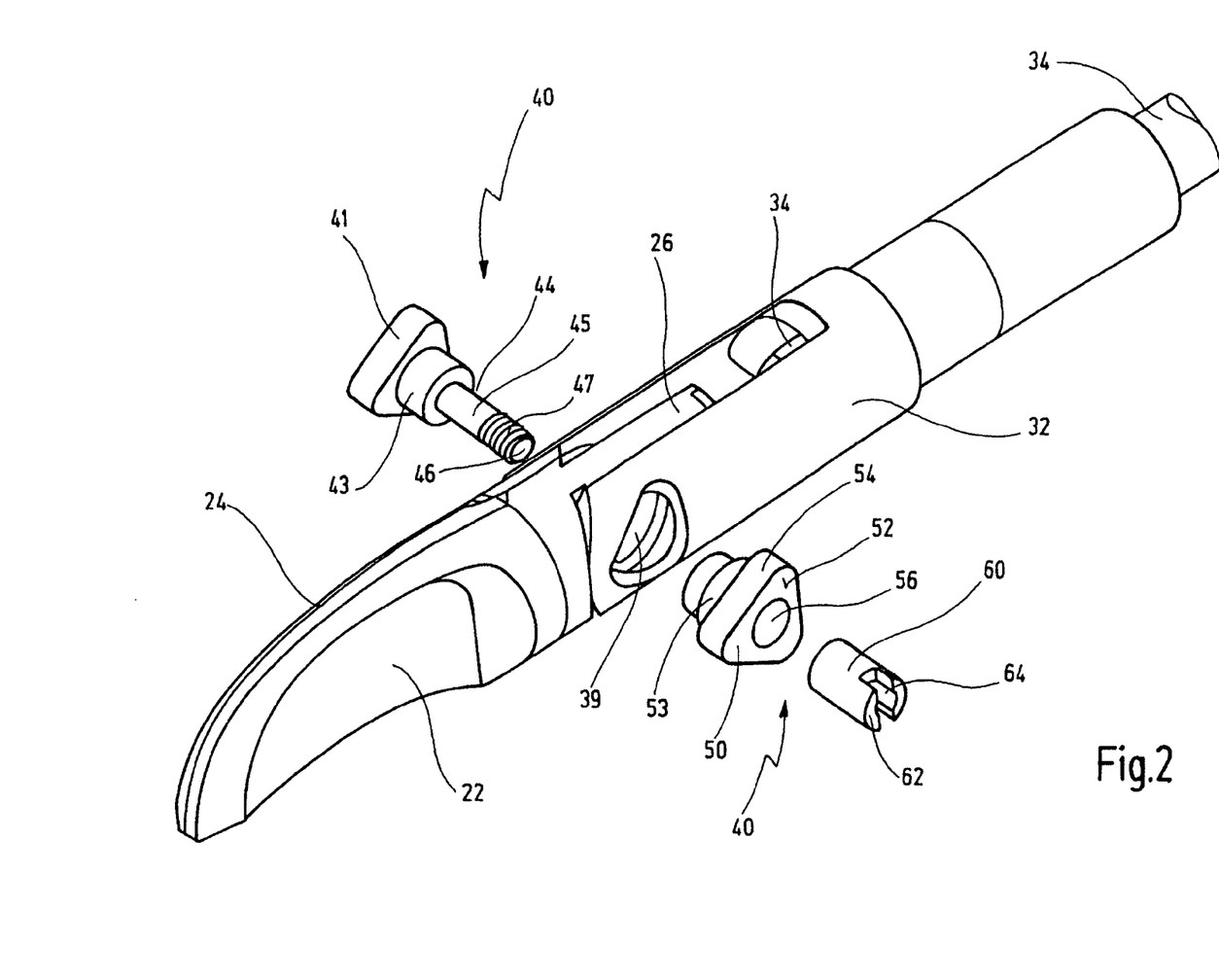
FIG. 2 shows a perspective view of a distal end area, with a multi-part axle pin seen in an exploded representation.
Figure 3:
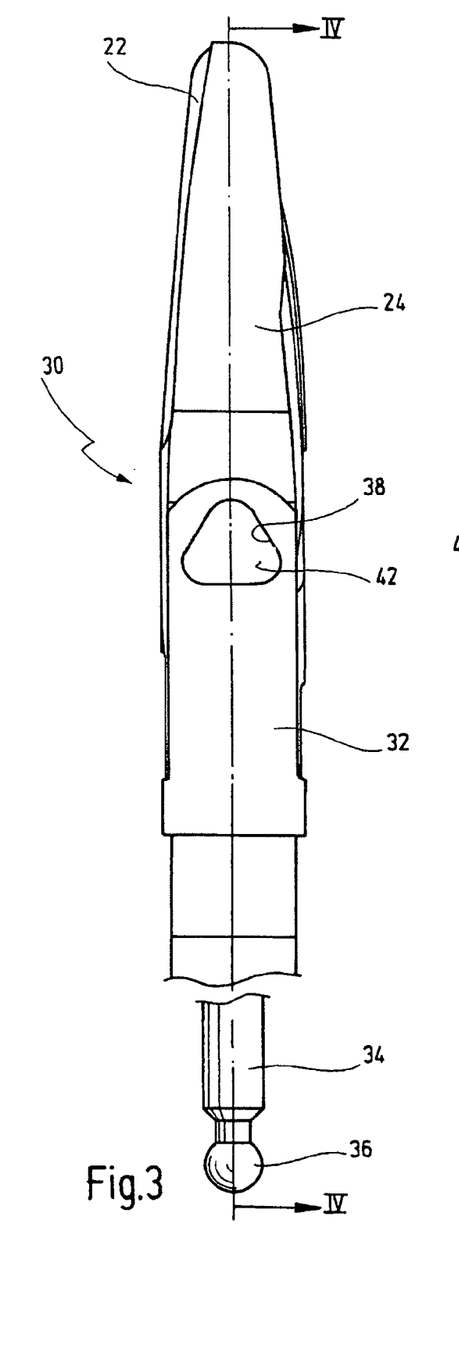
FIG. 3 shows a greatly enlarged and interrupted side view of the distal end area of the instrument from FIG. 1 with closed jaw parts, seen along the viewing direction III in FIG. 1.

The distal end area 30 of the shaft 12 is provided with a fork head 32, this fork head 32 having recessed openings 38, 39.

Figure 6:
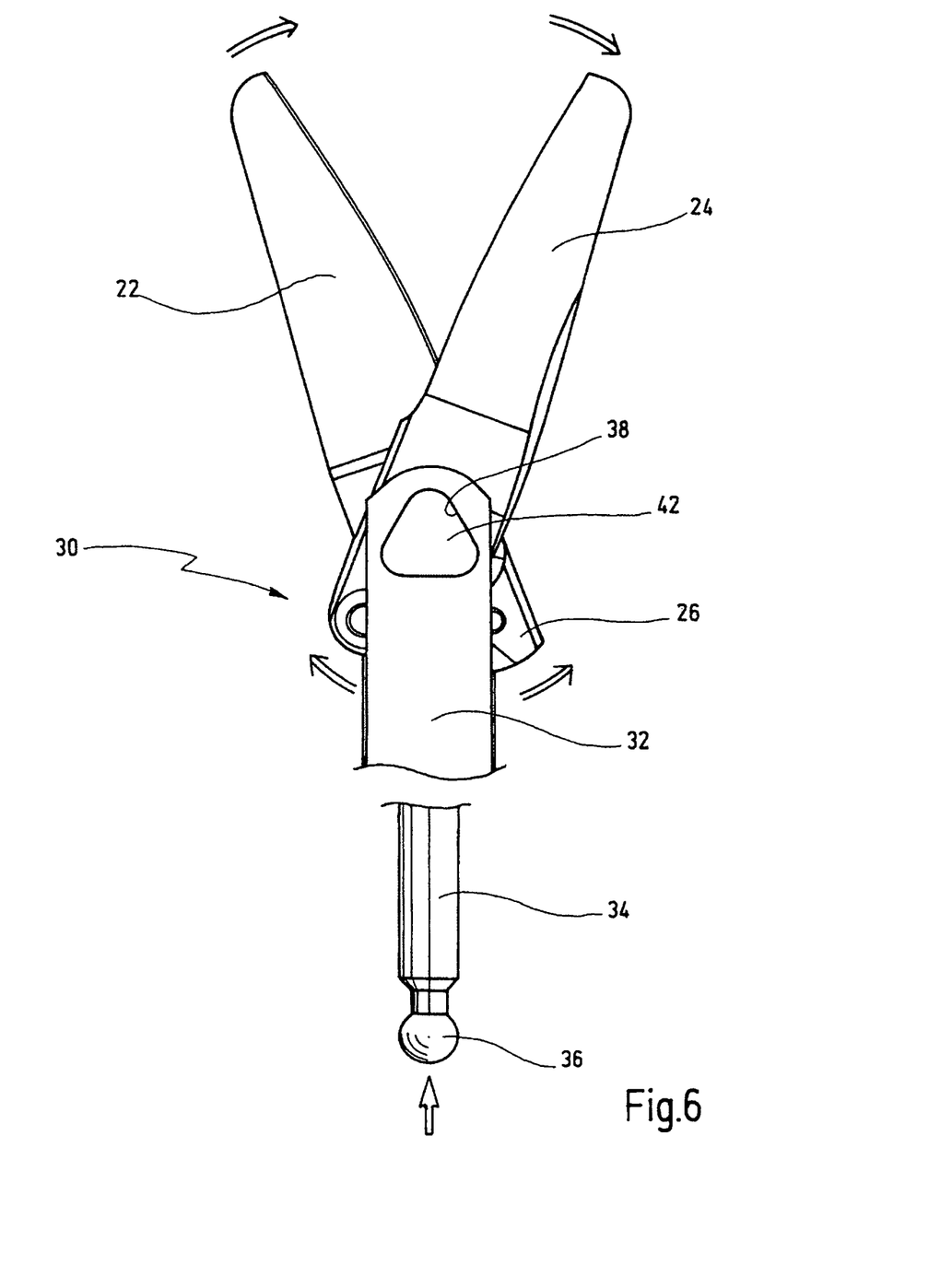
FIG. 6 shows a view, comparable to FIG. 3, with the jaw parts spread open.

In this fork head 32, a toggle mechanism 26 is received which at one end is connected to jaw parts 22, 24, as is shown in FIGS. 1 and 6.

These jaw parts 22, 24 are movable relative to one another and are arranged centrally between prongs of the fork head 32. Moreover, the jaw parts 22, 24 are mounted in the fork head 32 so as to be pivotable about an axle pin 40.

The multi-part configuration of the axle pin 40 is illustrated in the exploded drawing in FIG. 2.

The axle pin 40 is made up of three parts, namely a bolt 44, a bushing 50 and a tightening nut 60.

The bolt 44 has a triangular head 41, from whose underside a cylindrical shoulder 43 projects. This shoulder 43 merges into a peg 45 of smaller diameter with an external thread 47.

The bushing 50 has a triangular bushing head 54, from whose underside a cylindrical shoulder 53 projects. A through-opening 56 is also provided in the bushing 50.

The third component of the multi-part axle pin 40 is a tightening nut 60. This tightening nut 60 has a slit 64 and an internal thread (not visible here) which can be turned onto the external thread 47 of the bolt 44.

Figure 4:
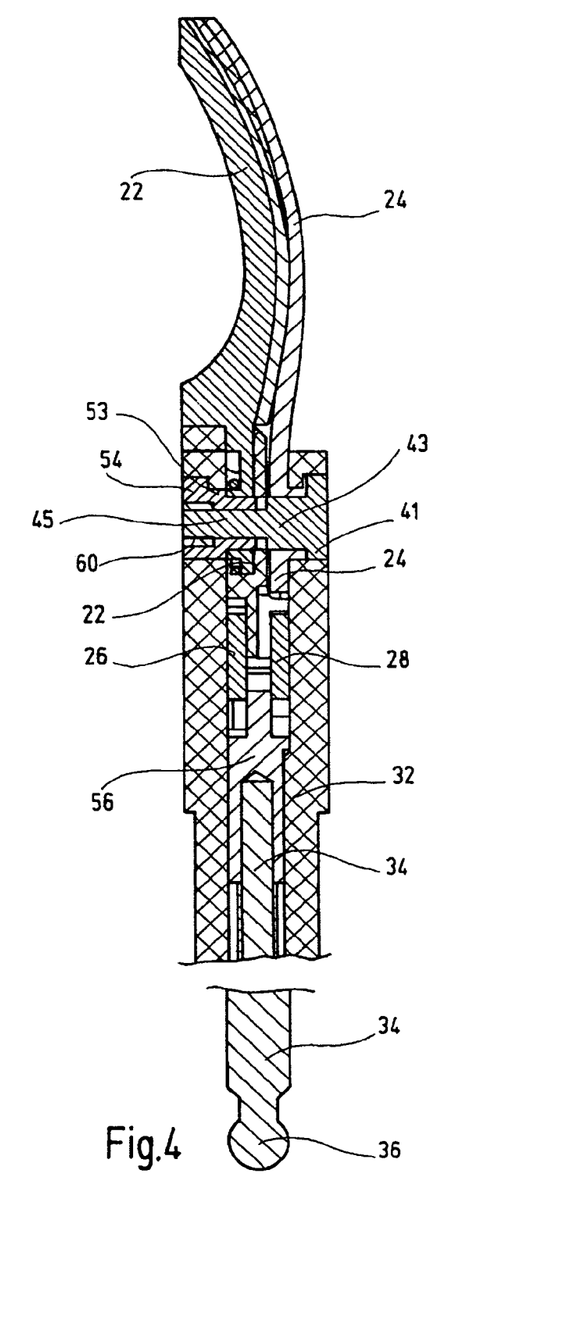
FIG. 4 shows a longitudinal section along the line IV-IV in FIG. 3.

The assembly of the multi-part axle pin 40 will be explained with reference to the exploded drawing in FIG. 2 and the sectional drawing in FIG. 4.

The bushing 50 is for this purpose forced with a press fit into the opening 39 of the fork head 32. The bolt 44 is then guided into the opening 38 of the fork head 32 from the opposite side and is pushed with its peg 45 into the opening 56 of the bushing 50. The tightening nut 60 is then screwed firmly to the screw thread 47 of the bolt 44. For this purpose, the tightening nut 60 has a slit 64 for engagement of a tool, for example a screwdriver.

After the axle pin 40 has been assembled, that part of the clamping nut 60 protruding beyond the outside of the fork is ground away (see FIG. 2).

At the end of this assembly step, only a tightening nut edge 62 can be seen externally in the viewing direction V in FIG. 1.

The use of a nonconductive material, for example plastic or ceramic, for the bushing 50 permits possible configurations of the medical instrument 10 for the field of electrocoagulation.

In the embodiment of the medical instrument 10 described here, the axle pin 40 comprises two components with heads which are in the form of equilateral triangles and have rounded triangle points. The contours and height of the recessed openings 38, 39 correspond to the heads 41, 54. In this way, the axle pin 40 is received both with an exact fit and flush in the fork head 32.

FIGS. 3 to 6 show a rod-shaped actuating element 34.

This rod-shaped actuating element 34 extends through the inside of the shaft 12 from the proximal end area 20 to the distal end area 30 of the medical instrument 10.

At its proximal end, the rod-shaped actuating element 34 is provided with a ball-shaped head 36. This ball-shaped head 36 is mounted in the housing 13 in a socket of the handle 14 (not visible here).

At the distal end area 30, the rod-shaped actuating element 34 is connected to the jaw parts 22, 24 via the toggle mechanism 26. The functioning of the rod-shaped actuating element 34 is indicated schematically in FIGS. 5 and 6 by double arrows and is explained in brief below.

Figure 5:
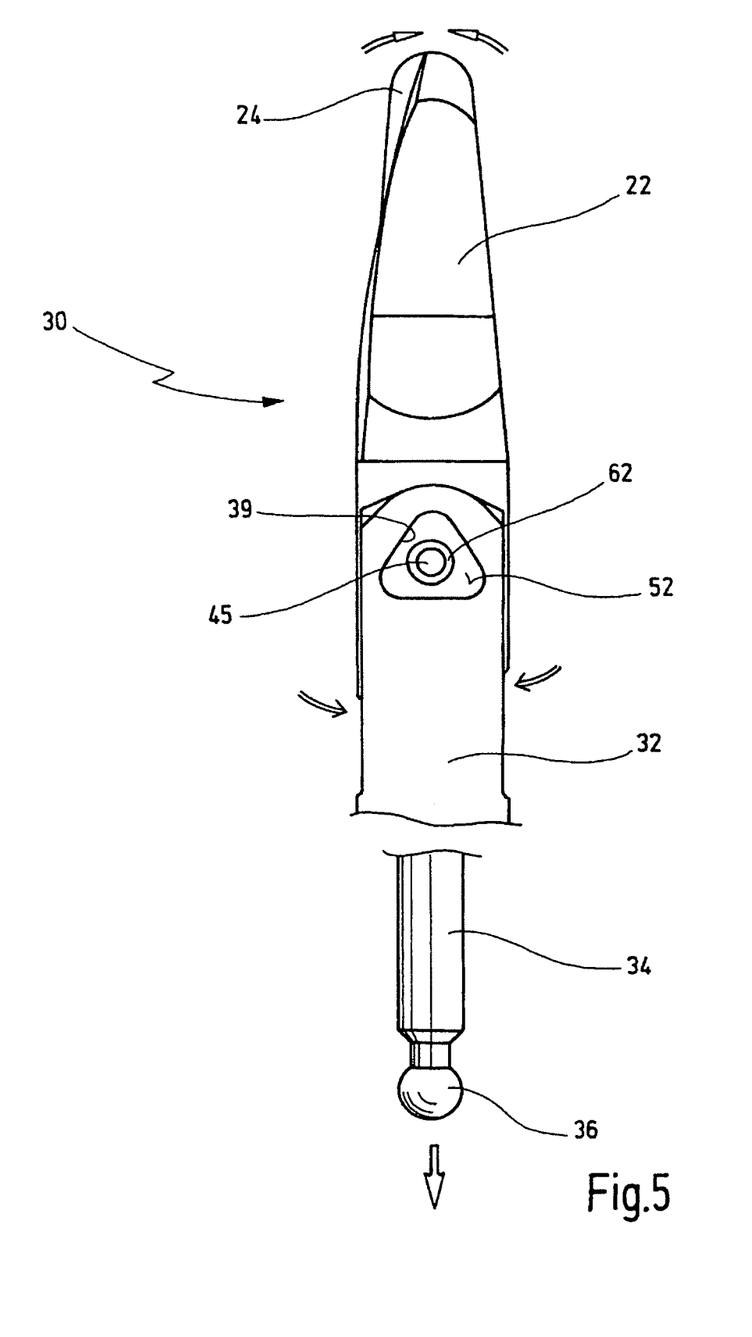
FIG. 5 shows a greatly enlarged side view, comparable to FIG. 3, of the distal end area with closed jaw parts, seen along the viewing direction V in FIG. 1.

A pivoting movement of the movable grip part 16 causes a linear movement of the rod-shaped actuating element 34. This takes place relative to the stationary grip part 15.

The shaft 12 in this case serves as a guide for the rod-shaped actuating element 34.

The linear movement of the rod-shaped actuating element 34 toward the distal end area 30 moves the toggle mechanism 26. In this way, the jaws 22, 24 are spread open.

When the grip parts 15, 16 are moved toward one another, i.e. closed, the rod-shaped actuating element 34 is displaced in the proximal direction. The toggle mechanism 26 is in this case moved such that the jaw parts 22, 24 are closed.

The forces that occur are taken up by the axle pin 40 and carried off via the contoured heads 41 and 54.

What is claimed is:

1. A medical instrument comprising
a distal end area,
jaw parts arranged at said distal end area which are movable relative to one another, and
an axle pin,
said jaw parts being pivotable about a circular section of said axle pin,
said axle pin being received in an opening at said distal end area,
wherein said axle pin comprises a head which is non-circular, and a contour of said opening corresponds to a contour of said head, said non-circular head in said opening secures said axle pin against rotation,
wherein said axle pin is made up of at least two components which can be joined to one another,
wherein said at least two components comprise a bushing and a bolt which can be inserted into said bushing,
wherein said at least two components which can be joined to one another composing said axle pin both have a non-circular head,
wherein said heads of said axle pin are respectively configured as a polygon;
wherein the corners of said polygon are rounded, and
wherein said distal end area of said medical instrument is designed as a fork head in whose opposite outer faces recessed openings are formed, into which said non-circular heads of said at least two components can be received in a way that said whole axle pin with said bushing and said bolt is received with an exact fit and flush in said fork head.

2. The medical instrument of claim 1, wherein said polygon is a triangle.

3. The medical instrument of claim 2, wherein said triangle is equilateral.

4. The medical instrument of claim 1, wherein said bolt and said bushing can be screwed together.

5. The medical instrument of claim 1, wherein said bolt and said bushing can be riveted together.

6. The medical instrument of claim 1, wherein a tightening nut is provided which can be placed between said bolt and said bushing in order to connect these parts one to another in a captive manner.

7. The medical instrument of claim 1, wherein a depth of said recessed openings corresponds to a height of said heads.

8. A medical instrument comprising
a distal end area;
jaw parts arranged at said distal end area which are movable relative to one another;
an axle pin including a bolt being generally circular and a head being non-circular;
said jaw parts being pivotable about said axle pin;
said distal end area having an opening for receiving said axle pin; and
said opening having a non-circular shape corresponding to said head for receiving said head in said opening,
wherein said axle pin is made up of at least two components which can be joined to one another,
wherein said at least two components comprise a bushing and the bolt which can be inserted into said bushing,
wherein said at least two components which can be joined to one another composing said axle pin both have a non-circular head, wherein said heads of said axle pin are respectively configured as a polygon;
wherein the corners of said polygon are rounded, and
wherein said distal end area of said medical instrument is designed as a fork head in whose opposite outer faces recessed openings are formed, into which said non-circular heads of said at least two components can be received in a way that said whole axle pin with said bushing and said bolt is received with an exact fit and flush in said fork head.

* * * * *